US007432091B2

(12) United States Patent
Yukawa et al.

(10) Patent No.: US 7,432,091 B2
(45) Date of Patent: Oct. 7, 2008

(54) HIGHLY EFFICIENT HYDROGEN PRODUCTION METHOD USING MICROORGANISM

(75) Inventors: Hideaki Yukawa, Soraku-gun (JP); Noriyuki Yamamoto, Kashiba (JP)

(73) Assignees: Research Institute of Innovative Technology for the Earth, Kyoto (JP); Sharp Corporation, Osaka (JP)

( * ) Notice: Subject to any disclaimer, the term of this patent is extended or adjusted under 35 U.S.C. 154(b) by 347 days.

(21) Appl. No.: 10/546,210

(22) PCT Filed: Feb. 23, 2004

(86) PCT No.: PCT/JP2004/002092

§ 371 (c)(1),
(2), (4) Date: Jan. 25, 2006

(87) PCT Pub. No.: WO2004/074495

PCT Pub. Date: Sep. 2, 2004

(65) Prior Publication Data

US 2006/0128001 A1    Jun. 15, 2006

(30) Foreign Application Priority Data

Feb. 24, 2003    (JP)    ............... 2003-046095

(51) Int. Cl.
*C12P 3/00* (2006.01)
*H01M 8/18* (2006.01)
(52) U.S. Cl. ............... 435/168; 429/19; 435/252.33; 435/252.8
(58) Field of Classification Search ............... None
See application file for complete search history.

(56) References Cited

U.S. PATENT DOCUMENTS

| 4,532,210 | A | 7/1985 | Miura et al. |
| 5,834,264 | A | 11/1998 | Sanford et al. |
| 6,395,521 | B1 | 5/2002 | Miura |
| 6,531,239 | B2 | 3/2003 | Heller |
| 6,686,075 | B2 | 2/2004 | Gieshoff et al. |
| 2002/0127440 | A1 | 9/2002 | Yamamoto et al. |

FOREIGN PATENT DOCUMENTS

| JP | 58-60992 | 4/1983 |
| JP | 61-205492 | 9/1986 |
| JP | 4-169178 | 6/1992 |
| JP | 7-218469 | 8/1995 |
| JP | 8-294396 | 11/1996 |
| JP | 10-064572 | 3/1998 |
| JP | 11-016588 | 1/1999 |
| JP | 2000-331702 | 11/2000 |
| JP | 2002-270209 | 9/2002 |
| JP | 2002-270210 | 9/2002 |
| JP | 2003-123821 | 4/2003 |
| JP | 2003-135088 | 5/2003 |

OTHER PUBLICATIONS

International Search Report of PCT/JP2004/002092, mailed May 25, 2004.
Larsson et al., "Kinetics of *Escherichia coli* hydrogen production during short term repeated aerobic-anaerobic fluctuation", Bioprocess Engineering, vol. 9, No. 4, 1993, pp. 167-172.
Tanisho et al., "Fermentative hydrogen evolution by *Enterobacter aerogenes* strain E. 82005", International Journal of Hydrogen Energy, vol. 12, issue 9, 1987, pp. 623-627.
Tanisho et al., "Microbial fuel cell using *Enterobacter aerogenes*", Journal of Electroanalytical Chemistry, vol. 275, 1989, pp. 25-32.
Nandi et al., "Involvement of anaerobic reductases in the spontaneous lysis of formate by immobilized cells of *Escherichia coli*", Enzyme and Microbial Technology, vol. 19, pp. 20-25, 1996.
Written Opinion of the International Searching Authority for PCT/JP2004/002092 dated May 6, 2004.
Kayukawa, The Nikkan Kogyo Shinbun, Ltd., Trigger, Jul. 2000, vol. 19, No. 7, pp. 14-16 and 116.
Nikkei Bio-tech, Nikkei Business Publications, Inc., Mikkei Latest Biotechnological Term Dictionary, 4th Edition, p. 346, Jun. 1995.
Palmore et al., "A methanol/dioxygen biofuel cell that uses NAD+-dependent dehydrogenases as catalysts", Journal of Electroanalytical Chemistry, vol. 443, pp. 155-161, 1998.
Suzuki et al, Applied Biochemistry and Bioengineering (1983) vol. 4, pp. 281-310.
Suzuki et al, Biotechnology and Bioengineering Symposium (1978)No. 8, pp. 501-511.
Karube et al, Biotechnology and Bioengineering (1977), vol. 19, No. 11, pp. 1727-1733.
ATCC Bacteria and Bacteriophages, American Type Culture Collection, 1996, Nineteenth Ed., pp. 142-143.
Peck, Jr. et al, "Formic Dehydrogenase and the Hydrogenlyase Enzyme Complex in Coli-Aerogenes Bacteria", J. Bacteriol., 1957, vol. 73, No. 6, pp. 706-721.
Bagramyan et al, The roles of hydrogenases 3 and 4, and the $F_0F_1$-ATPase, in $H_2$ production by *Escherichia coli* at alkaline and acidic pH, FEBS Letters, 2002, vol. 516, pp. 172-178.

*Primary Examiner*—Herbert J Lilling
(74) *Attorney, Agent, or Firm*—Nixon & Vanderhye P.C.

(57) ABSTRACT

It is intended to obtain anaerobic microbial cells in an amount sufficient for hydrogen generation reaction, impart a hydrogen generation function to an aerobic microorganism within a short time and provide an industrial advantageous method of producing hydrogen.

The above object can be established by providing a highly efficient microbial hydrogen production method characterized by comprising culturing a microorganism having a formate dehydrogenase gene and a hydrogenase gene under aerobic conditions, culturing the resulting microbial cells under anaerobic conditions in a liquid culture medium containing a formic acid compound, and then using the thus obtained cells for hydrogen generation.

17 Claims, No Drawings

US 7,432,091 B2

HIGHLY EFFICIENT HYDROGEN PRODUCTION METHOD USING MICROORGANISM

This application is the US national phase of international application PCT/JP2004/002092, filed 23 Feb. 2004, which designated the U.S. and claims priority of JP 2003-046095, filed 24 Feb. 2003, the entire contents of each of which are hereby incorporated by reference.

TECHNICAL FIELD

The present invention relates to a hydrogen production method using a microorganism, more particularly, a highly efficient hydrogen production method using an anaerobic microorganism utilizing an organic substrate as a carbon source. Hydrogen produced by the method of the present invention can be suitably used as a fuel of fuel cells, and the like.

BACKGROUND ART

Unlike fossil fuels, hydrogen is paid an attention as an ultimate clean energy source generating no substance which is feared in view of an environmental problem such as carbon dioxide gas and sulfur oxides even when fired, the calorie per unit mass of hydrogen is three times the colories of a petroleum, and when hydrogen is supplied to a fuel cell, it can be converted into electric energy and thermal energy at high efficiency.

For producing hydrogen, technique such as a method for thermal decomposition of water and steam-reforming of natural gas or naphtha has previously been proposed as a chemical process. Since this process requires the reaction conditions at high temperatures and pressures, and the synthetic gas produced contains CO (carbon monoxide), it becomes necessary to perform CO removal which is technically solved with difficulty, so as to prevent the deterioration in a fuel cell electrode catalyst, when such hydrogen is used as a fuel for fuel cells.

On the other hand, in a biological hydrogen production method using a microorganism, it is not necessary to remove CO, because such method has the reaction conditions at normal temperatures and pressures, and the generated gas does not contain CO.

From these aspects, biological hydrogen production using a microorganism is more preferable as a method of supplying a fuel for fuel cells.

Although the biological hydrogen production method has such excellent characteristics, a great progress has not been previously made as a method of supplying a fuel for fuel cells because such method has no economical practicability due to the productivity of hydrogen production, particularly a low hydrogen-generation rate (STY; Space Time Yield) per unit volume.

Biological hydrogen production methods are roughly classified into a method using a photosynthesis microorganism, and a method using a non-photosynthesis microorganism (mainly anaerobic microorganisms). Since the former method uses light energy for hydrogen generation, there are many problems to be solved such as cost of hydrogen generation apparatuses requiring a large light collecting area due to its low light energy utilization efficiency, and difficult maintenance and management, and this method is not at practical level.

The latter conventional hydrogen production method using an anaerobic microorganism relies on division and proliferation of the anaerobes. Anaerobic microorganisms have extremely slow division and proliferation (U.S. Pat. No. 5,834,264, and R. Nandi et al., Enzyme and Microbial Technology 19:20-25, 1996), and division and proliferation of anaerobic microorganisms require a greater free space necessary upon division and proliferation ("space" necessary for culturing, that is, proportionate to a reactor volume) as compared with that of other microorganisms although the reason has not been clarified. For this reason, the cell concentration in the stationary state that can be achieved by culturing of anaerobic microorganisms under anaerobic conditions necessary for hydrogen generation in the "space" of a fixed size is absolutely low as compared with that of other microorganisms. For these reasons, a hydrogen generation rate (STY) of anaerobic microorganisms is not sufficient. In this respect, significant improvement is demanded.

In addition, when hydrogen produced by a biological production method is supplied to a fuel cell of a constant electric capacity, it is practically necessary to make a supply of an organic substrate as a hydrogen source to a hydrogen generation reactor, and a rapid response of current generation. Also in this respect, technical solution is demanded.

DISCLOSURE OF THE INVENTION

The aforementioned problem of the previous hydrogen production method relying on division and proliferation of anaerobic microorganisms is, in other words, that the prior art could not find out a method which realizes to obtain a high density anaerobe in a hydrogen generation reactor and acquire hydrogen generation function of anaerobes at the same time in a short time.

An object of the present invention is to solve these technical problems regarding a hydrogen production method using an anaerobic microorganism. The object of the present invention is to obtain anaerobic microbial cells in an amount sufficient for hydrogen generation reaction, impart a hydrogen generation function to an anaerobic microorganism within a short time, and provide an industrially advantageous method of producing hydrogen. That is, an object of the present invention is to provide a method which has a sufficiently high hydrogen generation rate from the initial stage of the reaction, and can work a fuel cell at a practical level, not a method relying on division and proliferation of an anaerobic microorganism for a long time reaching 10-fold as described in the aforementioned US patent gazette.

Steps relating to the method of producing hydrogen according to the present invention include the following first to third steps.

That is, as a whole, the present invention comprises a first step of culturing particular microbial cells under aerobic conditions to proliferate microbial cells, a second step of culturing proliferated microbial cells in a culturing solution containing formic acids under anaerobic conditions to impart hydrogen generation ability to the microbial cells, and a third step of adding microbial cells to which hydrogen generation ability has been imparted like this to a hydrogen generation solution in the reduced state, and supplying an organic substrate to generate hydrogen.

As a metabolic pathway associated with hydrogen generation in anaerobic microorganisms, various pathways are known (pathways such as generation of hydrogen as a metabolite in a degradation pathway of glucose to pyruvic acid, generation of hydrogen as a metabolite in a pathway of producing acetic acid from pyruvic acid via acetyl CoA, and generation of hydrogen from formic acid derived from pyruvic acid). The present invention relates to a biological hydrogen production method utilizing a metabolic pathway of producing hydrogen from formic acid in a microorganism cell in the third step.

An object of the first step of the present invention is to proliferate and divide the aforementioned particular microbial cells by culturing the microbial cells under aerobic conditions, thereby to obtain the number of microbial cells required for hydrogen generation. However, microbial cells which have been cultured under aerobic conditions have no hydrogen generation ability. Since ethanol, acetic acid and lactic acid produced in the aerobic culture show inhibitory effect on the expression of hydrogen generation function of anaerobic microorganisms in the third step, it is preferable to recover the microbial cells from an aerobic culture solution before subjecting to the second step.

Regarding the second step, even if division and proliferation are not repeated many times under anaerobic conditions (hydrogen generation while repeating division many times is the conventional hydrogen generation method wherein the division and proliferation are relied upon), hydrogen generation function can be expressed by dividing and proliferating a microorganism about once in a formic acid-containing culture solution under anaerobic conditions. Although the reason why function can be expressed by about one time division and proliferation is not clear, the present inventors presume as follows:

Enzyme proteins involved in the pathway of producing hydrogen from formic acid are a formate dehydrogenase and a hydrogenase. These enzyme proteins usually function as a pair of units, and are present in the memrane or they are partially embedded in the membrane of microbial cells. As to conversion from the state where the unit function is not expressed as in aerobic division and proliferation into the state where the unit function is expressed, construction of the function for hydrogen generation of the aforementioned pair of units is completed by at least about one time division and proliferation of the microorganisms. Since the presence of oxygen has extremely great inhibiting effect on this construction, strict management of anaerobic conditions is required.

In addition, the third step of the present invention is different from the prior art in hydrogen generation, and relates to a method not relying on division and proliferation of a microorganism used, that is, a highly efficient hydrogen production method wherein division and proliferation of a microorganism in a hydrogen generation reaction are suspended or substantially suspended.

This highly efficient hydrogen production technique under suspension of division and proliferation is based on the aforementioned conclusion from detailed discussion of results of various studies which were practiced by the present inventors using a microorganism having a formate dehydrogenase gene and a hydrogenase gene. Of course, the present invention is not limited to this discussion contents.

Based on the aforementioned conclusion, the present inventors further studied intensively and, as a result, found out a method which is used at a high density in a hydrogen generation reactor, that is, a method of industrially advantageously realizing to obtain an anaerobic microorganism in a sufficient number of microbial cells and obtaining of hydrogen generation function of an anaerobic microorganism within a short time as well as efficient hydrogen generation, and found out that this technique can work a fuel cell at a practical level, which resulted in the present invention.

That is, the present invention relates to:

(1) a highly efficient microbial hydrogen production method characterized by comprising culturing a microorganism having a formate dehydrogenase gene and a hydrogenase gene under aerobic conditions, culturing the resulting microbial cells under anaerobic conditions in a liquid culture medium containing a formic acid compound, and then using the thus obtained cells for hydrogen generation, (2) a highly efficient microbial hydrogen production method characterized by comprising culturing a microorganism having a formate dehydrogenase gene and a hydrogenase gene under aerobic conditions, culturing the resulting microbial cells under anaerobic conditions in a liquid culture medium containing a formic acid compound to increase the number of microbial cells by at least 2-fold, and then using the thus obtained cells for hydrogen generation, (3) a highly efficient biological hydrogen production method characterized by comprising adding the microbial cells obtained by the method as defined in (1) or (2) to a solution for hydrogen generation in the reduced state, and supplying an organic substrate to the solution to generate hydrogen, (4) a highly efficient biological hydrogen production method characterized by comprising recovering the microbial cells obtained by the method as defined in (1) or (2), adding the recovered microbial cells to a solution for hydrogen generation in the reduced state, and continuously supplying an organic substrate to the solution to generate hydrogen, (5) the highly biological hydrogen production method according to (1) or (2), wherein the oxidation-reduction potential of the above liquid culture medium containing a formic acid compound is maintained in a range of −200 millivolt to −500 millivolt during culturing under anaerobic conditions, (6) the highly efficient biological hydrogen production method according to (3) or (4), wherein the oxidation-reduction potential of the solution for hydrogen generation in the reduced state is in a range of −100 millivolt to −500 millivolt, (7) the highly efficient biological hydrogen production method according to (3) or (4), wherein the organic substrate is formic acid, a formic acid salt or a compound which can be converted into formic acid by metabolism in microbial cells, (8) the highly efficient biological hydrogen production method according to (3) or (4), wherein the concentration of microbial cells in the solution for hydrogen generation in the reduced state is 0.1% (w/w) to 80% (w/w) (based on wet mass of microbial cells), (9) the highly efficient biological hydrogen production method according to any one of (3) to (8), wherein the pH of the solution for hydrogen generation is retained at 5.0 to 9.0, and an organic substrate is continuously supplied,

(10) use of hydrogen produced by the method as defined in any one of (1) to (9) as a fuel for fuel cells,

(11) a microorganism having highly efficient biological hydrogen generation capability, obtained by culturing a microorganism having a formate dehydrogenase gene and a hydrogenase gene under aerobic conditions, culturing the resulting microbial cells in a liquid culture medium containing a formic acid compound under anaerobic conditions to increase the number of the microbial cells by at least 2-fold, and then recovering the said cells.

BEST MODE FOR CARRYING OUT THE INVENTION

Microorganisms used in the invention are a microorganism having a formate dehydrogenase gene (F. Zinoni, et al., Proc. Natl. Acad. Sci. USA, Vol. 83, pp4650-4654, July 1986 Biochemistry) and a hydrogenase gene (R. Boehm, et al., Molecular Microbiology (1990) 4(2), 231-243), and is mainly an anaerobic microorganism.

Specific examples of an anaerobic microorganism used in the present invention include microorganisms of the genus *Escherichia*—for example, *Escherichia coli* ATCC9637, ATCC11775, ATCC4157, etc., microorganisms of the genus *Klebsiella*—for example, *Klebsiella pneumoniae* ATCC13883, ATCC8044, etc., microorganisms of the genus *Enterobacter*—for example, *Enterobacter aerogenes* ATCC13048, ATCC29007, etc., and microorganisms of the genus *Clostridium*—for example, *Clostridium beijerinckii* ATCC25752, ATCC17795, etc.

These anaerobic microorganisms are generally cultured first under aerobic conditions or anaerobic conditions, and the present inventors found that since division and proliferation under anaerobic conditions are extremely slow as compared with those under aerobic conditions, the first culture under aerobic conditions, followed by the second culture under anaerobic conditions are preferable. In this context, among anaerobic microorganisms, a facultative anaerobic microorganism (anaerobic microorganism which can survive under both of aerobic conditions and anaerobic conditions) is more suitably used than an obligate anaerobic microorganism (anaerobic microorganism which cannot survive under aerobic conditions). Among the aforementioned microorganisms, *Escherichia coli, Enterobacter aerogenes*, etc. are preferably used.

The culture under aerobic conditions at the first step can be performed using a conventional nutrient medium containing a carbon source, a nitrogen source, an inorganic salt, etc. In the culturing, for example, glucose, and molasses can be used as a carbon source. As a nitrogen source, for example, ammonia, ammonium sulfate, ammonium chloride, ammonium nitrate, and urea can be used alone or in combination thereof. In addition, as am inorganic salt, for example, potassium monohydrogen phosphate, potassium dihydrogen phosphate, and magnesium sulfate can be used. Besides, if necessary, nutrients such as peptone, meat extract, yeast extract, corn steep liquor, casamino acid, and various vitamins such as biotin and thiamine may be appropriately added to a medium.

The culturing can be usually performed at a temperature of about 20° C. to about 40° C., preferably about 25° C. to about 40° C. under aerobic conditions such as aerated agitation and shaking. In the culturing, the pH is adjusted to around 5 to 10, preferably around 6 to 8, and such pH adjustment during the culturing can be performed by adding an acid or an alkali. The concentration of a carbon source at the initiation of the culturing is 0.1 to 20% (W/V), preferably 1 to 5% (W/V). Further, the culturing time is usually a half day to 5 days. The number of microbial cells obtained by the first step is increased, but the microbial cells have no hydrogen generation capability.

Next, in a second step, the microbial cells which have been cultured in the first step like this are preferably separated and recovered from the culture solution once, and are then used in the second step. It is preferable that microbial cells which have been proliferated under aerobic conditions are separated from the culture solution containing a component inhibiting hydrogen generation (e.g. ethanol, acetic acid, lactic acid, etc.). However, the microbial cells proliferated under aerobic conditions have no hydrogen generation capability. Examples of separation include centrifugal separation, and filtration. Recovered microbial cells are cultured under anaerobic conditions by suspending in a liquid culture medium containing a formic acid compound (hydrogen generation capability-inducing medium), thereby to impart hydrogen generation capability to microbial cells. That is, hydrogen generation capability is imparted to microbial cells at the second step. It is preferable that microbial cells are usually recovered after the number of microbial cells has been increased at least 2-fold or more. Herein, examples of the formic acid compound to be contained in an induction medium include formic acid and a formic acid salt (e.g. sodium formate), and it is preferable that such formic acid compound is generally contained at about 1 mM to 50 mM (millimolar) per 1 L of a liquid culture medium.

The present procedure is performed for the purpose of inducing and expressing the function of a unit comprising formate dehydrogenase and hydrogenase in microorganism cells used under anaerobic conditions. For such purpose, it is preferable requirements to perform the procedure under management of strict anaerobic conditions in a liquid culture medium containing a formic acid compound. It is enough that a preferable extent of division and proliferation, that is, increase in the number of cells to around 2-fold extent or more may be confirmed. This extent of division and proliferation can be easily known by performing the conventional measurement of the optical density of microbial cells, for example, measurement with a spectrophotometer DU-800 manufactured by Beckman Coulter.

Regarding a composition of an induction medium of a formic acid compound-containing liquid culture medium, it is preferable to satisfy the conditions under which microorganism cells to be used can be divided at least around once, but division and proliferation of microbial cells are not necessarily essential, and impartation of hydrogen generation capability to microbial cells by culturing induction is essential. To mention additionally, it is preferable conditions that a trace metal component (a necessary metal component is different depending on a microorganism species to be used, and is generally iron, molybdenum, etc.) necessary for inducing and expressing formate dehydrogenase and hydrogenase is contained. In addition, since this trace metal component is contained in a natural nutrient source (e.g. yeast extract, corn steep liquor, beef extract, fish extract, etc.) usually used in a microorganism culturing component to a considerable extent, it is not necessarily required to add the trace metal component separately, in some cases.

In order that microorganism cells are divided, a carbon source is also a necessary component. In this source, sugars such as glucose, organic acids, and alcohols are usually used. In this case, it should be noted that, depending on the species of microorganisms used, hydrogen generation capability suppressed by a carbon source such as glucose present in a culture medium, that is, so-called glucose suppressing effect is seen in some cases. In this case, it is preferable to use a carbon source such as glucose at a necessary amount for around one time division of microorganism cells used. The amount can be easily determined by a person skilled in the art. In addition to a carbon source, a nitrogen source (ammonium sulfate, ammonium nitrate, ammonium phosphate, etc.), phosphorus, potassium, etc. are added if necessary.

Specifically, for example, culturing is performed using a formic acid compound-containing liquid culture medium having the following composition (induction medium composition) relative to an amount of around 30 g (gram) (wet mass) of microbial cells obtained by aerobic culture.

TABLE 1

Induction medium composition

| Composition component | Concentration |
| --- | --- |
| Water | 1000 ml (milliliter) |
| Yeast extract | 0.5% |

TABLE 1-continued

Induction medium composition

| Composition component | Concentration |
| --- | --- |
| Tryptone peptone | 1.0% |
| Anhydrous sodium molybdate | μM (micromole) |
| Sodium selenite pentahydrate | μM (micromole) |
| Sodium secondary phosphate | 26.5 mM (millimole) |
| Sodium primary phosphate | 73.5 mM (millimole) |
| Glucose | 20 mM (millimole) |
| Sodium sulfate | 0.05% |
| Sodium formate | 5 mM (millimole) |

In the present invention, unless otherwise indicated, % is expressed in terms of % by weight.

With respect to realization of anaerobic conditions for imparting hydrogen generation capability to microbial cells at the present second step, the known method may be used. For example, an aqueous solution of desired anaerobic conditions may be obtained by referring to the method of preparing a liquid culture medium for sulfate-reducing microorganisms (Pfennig, N et al. (1981): The dissimilatory sulfate-reducing bacteria, In The Prokaryotes, A Handbook on Habitats, Isolation and Identification of Bacteria, Ed. by Starr. M. P. et al., P. 926-940, Berlin, Springer Verlag, and "Agricultural Chemistry Experimental Protocol, vol. 3, Ed. by Kyoto University, Faculty of Agriculture, Division of Agricultural Chemistry, 1990, 26 impression, published by Sangyo-Tosho Publishing Co.").

Specifically, it is preferable that, before use in the culturing, a dissolved gas is removed by treating an aqueous solution for an induction medium under reduced pressure. More specifically, by treating an induction medium under reduced pressure at about $13.33 \times 10^2$ Pa or lower, preferably about $6.67 \times 10^2$ Pa or lower, more preferably about $4.00 \times 10^2$ Pa or lower for about 1 to 60 minutes, preferably 5 to 60 minutes, a dissolved gas, particularly dissolved oxygen is removed, thereby to prepare an induction medium at the anaerobic state. During the treatment under reduced pressure, heating treatment may be performed if desired. The heating temperature is usually about 80° C. to 150° C. Since such treatment removes oxygen, it is useful for making anaerobic conditions.

Alternatively, an aqueous solution used as a liquid culture medium of anaerobic conditions at the second step may be prepared optionally by adding a suitable reducing agent (e.g. thioglycolic acid, ascorbic acid, cysteine hydrochloride, mercaptoacetic acid, thiolacetic acid, glutathione, sodium sulfide, etc.) to an aqueous solution (e.g. aqueous solutions in Table 1). Alternatively, according to circumstances, it is an effective method of preparing an aqueous solution of the anaerobic state to appropriately combine these methods.

The anaerobic state of an induction medium can be simply presumed by a resazurin indicator (decoloration from blue to colorless) to some extent, and can be specified by an oxidation-reduction potential measured by an oxidation-reduction potentiometer (e.g. ORP Electrodes manufactured by BROADLEY JAMES). An oxidation-reduction potential of an induction medium in which the anaerobic state is maintained is preferably about −200 mV to −500 mV, more preferably about −250 mV to −500 mV.

For maintaining the anaerobic state during the reaction, it is desirable to prevent as much as possible the mixing of oxygen from the outside of the reaction system, and a method of sealing a reaction system with an inert gas such as nitrogen gas and carbon dioxide gas is usually used.

Upon expression of unit function of enzyme proteins, it becomes necessary in some cases to add an adjusting solution for maintaining the pH of the reaction system and appropriately add various nutrient-dissolved solutions, in order to function metabolic function in microbial cells more effectively. In such case, in order to prevent the mixing of oxygen inhibiting function expression, it is effective to remove oxygen from the solution to be added in advance.

The time and temperature required for division and proliferation to 2-fold or more the number of microbial cells in the present step, that is, the time and temperature necessary for expressing unit function of desired enzyme proteins are conditions of 5 hours to 24 hours, and 25° C. to 40° C. The pH of the liquid culture medium in the culturing of microbial cells is usually about 5.0 to 9.0.

A method of recovering microbial cells having desired function like this is not particularly limited, but the known method such as centrifugation and membrane separation can be used.

Subsequently, in the third step, the microbial cells having hydrogen generation capability, which have been recovered and separated as described above, are added to a solution for hydrogen generation in the reduced state, and an organic substrate is supplied to a biological hydrogen production method continuously or intermittently. It is preferable that an organic substrate is continuously supplied and, when supplied intermittently, it is required that a sufficient amount for hydrogen generation is present in the reaction system. As a use form of the recovered microbial cells, such cells may be used without any treatment, or they are immobilized with acrylamide, carrageenan or the like and then used.

As to recovery and separation of microbial cells, the method of culturing microbial cells aerobically and further anaerobically, separating and recovering the microbial cells once after they acquire unit function of hydrogen generation, and adding the said cells to a solution for hydrogen generation to generate hydrogen under reduced state, as according to the present invention, is more preferable for exerting the effect of the method of the present invention than the method where the aerobically cultured microbial cells are directly used for hydrogen generation under reduced state.

As a solution for hydrogen generation, there is used a solution having the same as or similar to the composition of an induction medium solution used in the second step. However, since hydrogen generation is vigorous, it is recommended to use an anti-foaming agent (commercially available anti-foaming agent, for example, a silicone-based anti-foaming agent, a polyether-based anti-foaming agent, etc.).

Microbial cells are used at a concentration of about 0.1% (w/w) to 80% (w/w) (based on wet mass of microbial cells), preferably about 5% (w/w) to 70% (w/w) (based on wet mass of microbial cells), more preferably about 10% (w/w/) to 70% (w/w) (based on wet mass of microbial cells).

Regarding the composition of a solution for hydrogen generation, a medium having a similar composition to that of the hydrogen generation ability-inducing medium at the second step is used. A reducing agent may also be used as in the second step. However, since proliferation of microbial cells is not caused, carbohydrates in the necessary amount for proliferating microbial cells are not usually contained in the above liquid composition. In this case, since it is an important point not to substantially proliferate microbial cells, a carbon source such as glucose used for proliferating microbial cells is not necessary in the medium. Even if a carbon source is used, only a necessary amount for maintaining hydrogen generation capability of microbial cells is enough (because the present invention is a biological hydrogen production method with cells which have substantially stopped proliferation).

Specifically, culturing is usually performed using a solution for hydrogen generation having the following composition relative to an amount of about 800 g (gram) (wet mass) of microbial cells.

TABLE 2

Composition of solution for hydrogen generation

| Composition component | Concentration |
| --- | --- |
| Water | 1000 ml (milliliter) |
| Yeast extract | 0.5% |
| Tryptone peptone | 1.0% |
| Anhydrous sodium molybdate | μM (micromole) |
| Sodium selenite pentahydrate | μM (micromole) |
| Sodium secondary phosphate | 26.5 mM (millimole) |
| Sodium primary phosphate | 73.5 mM (millimole) |
| Anti-foaming agent (Antifoam (manufactured by Wako Pure Chemical Industries. Ltd.)) | 0.1% |

The reduced state of a solution for hydrogen generation can be realized according to a method of realizing the aforementioned anaerobic conditions of a formic acid compound-containing liquid culture medium. The reduced state of a solution for hydrogen generation is specified such that its oxidation-reduction potential is about −100 mV to −500 mV, more preferably −200 mV to −500 mV.

A formic acid compound is supplied not as a formic acid compound necessary for expressing induction of a protein function unit in the second step, but as an organic substrate necessary in a raw material for hydrogen generation in the third step. The formic acid compound which is an organic substrate continuously or intermittently supplied to a solution for hydrogen generation may be a compound which is converted into formic acid in the pathway occurring in the metabolism of microbial cells in a liquid culture medium (e.g. monosaccharide such as glucose, fructose, xylose, arabinose, etc., disaccharide such as sucrose, maltose, etc., molasses, etc.), or formic acid or a formic acid salt (e.g. sodium formate, potassium formate) which is directly supplied from the outside. An indirect supplying method using a compound capable of being changed into formic acid, and a direct supplying method may be used in combination thereof, but the direct supplying method from the outside is suitable. The amount and rate of an organic substrate which is continuously or intermittently supplied to a solution for hydrogen generation are not particularly limited as far as the pH of a solution is controlled in a range of about 5.0 to 9.0.

The hydrogen generation reaction is performed under the condition of about 20° C. to 40° C., preferably about 30° C. to 40° C.

The hydrogen generation container in which a hydrogen generation reaction is performed may be the previously known container.

According to the method of the present invention, a remarkably high hydrogen generation rate (STY), and rapid response to supply of an organic substrate and hydrogen generation can be realized, and the technique excellent as a format of supplying hydrogen for a fuel cell can be provided.

EXAMPLE

The present invention will be explained below by way of Examples, but the present invention is not limited to those Examples.

Example 1

Biological Hydrogen Production Method with *Escherichia coli* W Strain (ATCC 9637)

The present bacterial strain was added to 500 ml of a liquid culture medium having a composition shown by the following Table 3, and shake culture was performed at 37° C. overnight under aerobic conditions.

TABLE 3

Composition of aerobic culture medium (LB medium)

| Composition component | Amount of component |
| --- | --- |
| Water | 1000 ml |
| Tryptone | 10 g |
| Yeast extract | 5 g |
| Sodium chloride | 5 g |

Then, in order to remove influences due to aerobic culture, the present liquid culture medium was subjected to a centrifuge (5000 rpm, 15 min), and the bacterial cells obtained by separating from the liquid culture medium were suspended in 6 L (liter) of an induction medium for expressing the unit function of enzyme protein having the composition shown by Table 1 under anaerobic conditions.

The induction medium solution had been heated at 120° C. for 10 minutes in advance, dissolved oxygen had been immediately removed for 20 minutes under reduced pressure condition (about $4.00 \times 10^2$ Pa), and had been introduced in a glass container of an internal volume of 10 L (liter) equipped with a stirring device, a temperature maintaining device and an oxidation-reduction potential measuring device under the nitrogen atmosphere.

Qualitative confirmation of an anaerobic extent of an induction medium was performed by change in tone of a resazurin indicator (change from blue to colorless).

Culturing for induction-expressing the unit function of enzyme protein in the bacterial cells was performed at 30° C. for 2 hours under anaerobic conditions while stirring under the nitrogen atmosphere. During the induction culturing, an oxidation-reduction potential of the liquid culture medium was changed and maintained in the vicinity of −400 mV. In addition, when the bacterial cell concentration in an inducing liquid culture medium was measured with a spectrophotometer DU-800 manufactured by Beckman Coulter, the concentration was increased from the initial optical density ($OD_{610}$) of 1.5 to the final $OD_{610}$ of 3.7 in the bacterial cells. About 6500 g of the thus obtained induction liquid culture medium was subjected to a centrifuge (5000 rpm, 12 minutes) to recover the bacterial cells.

Then, the recovered bacterial cells were suspended in 50 ml of a solution for hydrogen generation under the reduced state which has the composition of Table 2 (bacterial cell concentration of about 40%, based on wet mass of bacterial cells).

The reactor of an internal volume of 200 ml for hydrogen generation was provided with a formic acid supplying nozzle, a stirring device, a pH adjusting device, a temperature maintaining device and an oxidation-reduction potential measuring device, and was fixed in a constant temperature water bath set at 37° C.

An aqueous formic acid solution having a concentration of 5 M (mole)/L (liter) was continuously supplied to a reactor at a feed rate of 16 ml/hr using a micro pump, and the amount of a generated gas was measured.

The pH in the system was controlled with a phosphate buffer at around 6.5, and the oxidation-reduction potential in the system was rapidly dropped from around −200 mV at the initial stage of the hydrogen generation reaction, and was maintained around −390 mV.

At the same time with supply of formic acid, gas generation occurred, and such gas generation was continued during continuous supply of formic acid (for about 6 hours of experimental time).

The gas generation rate measured with a gas flowmeter was an approximately constant average rate of 92 ml/min. and, when the collected gas was analyzed by gas chromatography, the generated gas contained 49% of hydrogen and the remaining carbon dioxide gas.

Therefore, the hydrogen generation rate is 54 L ($H_2$)/hr/L (reaction volume).

This hydrogen-generation rate has a capacity to immediately activate a decentralized installation type 1 KW fuel cell for home use when needed.

INDUSTRIAL APPLICABILITY

According to the present invention, by using a microorganism having a formate dehydrogenase gene and a hydrogenase gene, hydrogen useful for fuel cells can be supplied at a remarkably high hydrogen generation rate (STY), and a highly efficient biological hydrogen production method can be provided.

The invention claimed is:

1. A biological hydrogen production method comprising culturing a microorganism having a formate dehydrogenase gene and a hydrogenase gene under aerobic conditions to form a first cultured microorganism, culturing the first cultured microorganism in a liquid culture medium containing a formic acid compound under anaerobic conditions to form a second cultured microorganism, adding the second cultured microorganism to a solution for hydrogen generation in the reduced state, and supplying an organic substrate to generate hydrogen, wherein division and proliferation of the microbial cells are substantially suspended while generating hydrogen.

2. A biological hydrogen production method comprising culturing a microorganism having a formate dehydrogenase gene and a hydrogenase gene under aerobic conditions to form a first cultured microorganism, culturing the first cultured microorganism in a liquid culture medium containing a formic acid compound under anaerobic conditions to form a second cultured microorganism, recovering the microbial cells of the second cultured microorganism and adding the recovered microbial cells to a solution for hydrogen generation in the reduced state, and supplying an organic substrate to generate hydrogen, wherein division and proliferation of the microbial cells are substantially suspended while generating hydrogen.

3. A biological hydrogen production method comprising culturing a microorganism having a formate dehydrogenase gene and a hydrogenase gene under aerobic conditions to form a first cultured microorganism, culturing the first cultured microorganism under anaerobic conditions in a liquid culture medium containing a formic acid compound to form a second cultured microorganism with at least a two-fold increase in the number of microbial cells as compared to said first cultured microorganism, and using the second cultured microorganism for generating hydrogen.

4. The biological hydrogen production method according to claim 1, wherein the oxidation-reduction potential of the liquid culture medium containing a formic acid compound is maintained in a range of −200 millivolt to −500 millivolt during culturing under anaerobic conditions.

5. The biological hydrogen production method according to claim 2, wherein the oxidation-reduction potential of the liquid culture medium containing a formic acid compound is maintained in a range of −200 millivolt to −500 millivolt during culturing under anaerobic conditions.

6. The biological hydrogen production method according to claim 3, wherein the oxidation-reduction potential of the liquid culture medium containing a formic acid compound is maintained in a range of −200 millivolt to −500 millivolt during culturing under anaerobic conditions.

7. The biological hydrogen production method according to claim 1, wherein the oxidation-reduction potential of the solution for hydrogen generation in the reduced state is in a range of −100 millivolt to −500 millivolt.

8. The biological hydrogen production method according to claim 2, wherein the oxidation-reduction potential of the solution for hydrogen generation in the reduced state is in a range of −100 millivolt to −500 millivolt.

9. The biological hydrogen production method according to claim 1, wherein the organic substrate is formic acid, a formic acid salt, or a compound which can be converted into formic acid by metabolism in microbial cells.

10. The biological hydrogen production method according to claim 2, wherein the organic substrate is formic acid, a formic acid salt, or a compound which can be converted into formic acid by metabolism in microbial cells.

11. The biological hydrogen production method according to claim 1, wherein the concentration of microbial cells in the solution for hydrogen generation in the reduced state is 0.1% (w/w) to 80% (w/w), based on wet mass of microbial cells.

12. The biological hydrogen production method according to claim 2, wherein the concentration of microbial cells in the solution for hydrogen generation in the reduced state is 0.1% (w/w) to 80% (w/w), based on wet mass of microbial cells.

13. The biological hydrogen production method according to claim 1, wherein the pH of the solution for hydrogen generation is retained at 5.0 to 9.0, and an organic substrate is continuously supplied.

14. The biological hydrogen production method according to claim 2, wherein the pH of the solution for hydrogen generation is retained at 5.0 to 9.0, and an organic substrate is continuously supplied.

15. A biological hydrogen production method comprising culturing *Escherichia coli* W strain (ATCC9637) having a formate dehydrogenase gene and a hydrogenase gene under aerobic conditions to form a first cultured microorganism, culturing the first cultured microorganism in a liquid culture medium containing formic acid salt under anaerobic conditions to form a second cultured microorganism, adding the second cultured microorganism to a solution for hydrogen generation in the reduced state, and supplying formic acid to generate hydrogen, wherein division and proliferation of the microbial cells are substantially suspended while generating hydrogen.

16. A biological hydrogen production method comprising culturing *Escherichia coli* W strain (ATCC9637) having a formate dehydrogenase gene and a hydrogenase gene under aerobic conditions to form a first cultured microorganism, culturing the first cultured microorganism in a liquid culture medium containing formic acid salt under anaerobic conditions to form a second cultured microorganism, recovering the microbial cells of the second cultured microorganism and adding the recovered microbial cells to a solution for hydrogen generation in the reduced state, and supplying formic acid to generate hydrogen, wherein division and proliferation of the microbial cells are substantially suspended while generating hydrogen.

17. A biological hydrogen production method comprising culturing *Escherichia coli* W strain (ATCC9637) having a formate dehydrogenase gene and a hydrogenase gene under aerobic conditions to form a first cultured microorganism, culturing the first cultured microorganism under anaerobic conditions in a liquid culture medium containing formic acid salt to form a second cultured microorganism with at least a two-fold increase in the number of microbial cells as compared to said first cultured microorganism, and using the second cultured microorganism for generating hydrogen.

* * * * *